United States Patent
Chinn et al.

(10) Patent No.: US 8,666,510 B2
(45) Date of Patent: *Mar. 4, 2014

(54) LEAD CONNECTION SYSTEM FOR AN IMPLANTABLE ELECTRICAL STIMULATION SYSTEM AND METHODS FOR MAKING AND USING THE SYSTEMS

(71) Applicant: Boston Scientific Neuromodulation Corporation, Valencia, CA (US)

(72) Inventors: Kenny Kinyen Chinn, Beaverton, OR (US); John Michael Barker, Ventura, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/020,340

(22) Filed: Sep. 6, 2013

(65) Prior Publication Data

US 2014/0012358 A1    Jan. 9, 2014

Related U.S. Application Data

(63) Continuation of application No. 12/210,600, filed on Sep. 18, 2008, now Pat. No. 8,548,601.

(51) Int. Cl.
*A61N 1/00* (2006.01)
*H01R 13/625* (2006.01)

(52) U.S. Cl.
USPC ............ 607/116; 607/27; 607/117; 607/119; 607/152; 439/347; 439/909

(58) Field of Classification Search
USPC .................... 607/27, 38, 116, 117, 119, 152; 439/347, 909
See application file for complete search history.

(56) References Cited

U.S. PATENT DOCUMENTS 3,908,668 A    9/1975    Bolduc
3,951,154 A    4/1976    Hartlaub
(Continued)

FOREIGN PATENT DOCUMENTS

EP    1479133 A1    11/2004
WO    9510324 A1    4/1995
(Continued)

OTHER PUBLICATIONS

U.S. Appl. No. 12/210,600 Official Communication dated Dec. 29, 2011.

(Continued)

*Primary Examiner* — Niketa Patel
*Assistant Examiner* — William Levicky
(74) *Attorney, Agent, or Firm* — Frommer Lawrence & Haug LLP

(57) ABSTRACT

A lead connection system includes a connector housing. A plurality of lead retainers disposed in the connector housing are configured and arranged to removably attach to a proximal end of one of a received plurality of leads. The plurality of lead retainers include at least one of a slidable drawer and at least one pivotable hinged panel. A plurality of connector contacts are configured and arranged for making electrical contact with one or more of the terminals of one or more of the plurality of received leads. A single connector cable has a distal end that is electrically coupled to the plurality of connector contacts and a proximal end that is configured and arranged for insertion into a trial stimulator. A cable connector is electrically coupled, via the connector contacts, to at least one terminal of each of the received plurality of leads.

20 Claims, 11 Drawing Sheets

(56) References Cited

U.S. PATENT DOCUMENTS

| | | |
|---|---|---|
| 4,044,775 A | 8/1977 | McNichols |
| 4,124,029 A | 11/1978 | Penn |
| 4,245,642 A | 1/1981 | Skubitz et al. |
| 4,278,093 A | 7/1981 | Lafortune et al. |
| 4,466,441 A | 8/1984 | Skubitz et al. |
| 4,784,141 A | 11/1988 | Peers-Trevarton |
| 5,174,303 A | 12/1992 | Schroeppel |
| 5,241,957 A | 9/1993 | Camps et al. |
| 5,324,312 A | 6/1994 | Stokes et al. |
| 5,330,521 A | 7/1994 | Cohen |
| 5,374,279 A | 12/1994 | Duffin, Jr. et al. |
| 5,431,695 A | 7/1995 | Wiklund et al. |
| 5,489,225 A | 2/1996 | Julian |
| 5,497,771 A | 3/1996 | Rosenheimer |
| 5,509,822 A | 4/1996 | Negus et al. |
| 5,534,019 A | 7/1996 | Paspa |
| 5,545,189 A | 8/1996 | Fayram |
| 5,582,180 A | 12/1996 | Manset et al. |
| 5,620,477 A | 4/1997 | Pless et al. |
| 5,637,417 A | 6/1997 | Engmark et al. |
| 5,679,026 A | 10/1997 | Fain et al. |
| 5,683,433 A | 11/1997 | Carson |
| 5,755,763 A | 5/1998 | Farfel |
| 5,782,892 A | 7/1998 | Castle et al. |
| 5,837,006 A | 11/1998 | Ocel et al. |
| 5,871,508 A | 2/1999 | Thompson et al. |
| 5,931,861 A | 8/1999 | Werner et al. |
| 6,167,314 A | 12/2000 | Fischer, Sr. et al. |
| 6,181,969 B1 | 1/2001 | Gord |
| 6,317,633 B1 | 11/2001 | Jorgenson et al. |
| 6,397,108 B1 | 5/2002 | Camps et al. |
| 6,445,954 B1 | 9/2002 | Olive et al. |
| 6,505,073 B2 | 1/2003 | Gramse |
| 6,516,227 B1 | 2/2003 | Meadows et al. |
| 6,609,029 B1 | 8/2003 | Mann et al. |
| 6,609,032 B1 | 8/2003 | Woods et al. |
| 6,620,186 B2 | 9/2003 | Saphon et al. |
| 6,662,035 B2 | 12/2003 | Sochor |
| 6,671,534 B2 | 12/2003 | Putz |
| 6,671,553 B1 | 12/2003 | Helland et al. |
| 6,741,892 B1 | 5/2004 | Meadows et al. |
| 6,854,994 B2 | 2/2005 | Stein et al. |
| 6,879,857 B2 | 4/2005 | Swanson et al. |
| 6,895,276 B2 | 5/2005 | Kast et al. |
| 6,968,235 B2 | 11/2005 | Belden et al. |
| 7,047,077 B2 | 5/2006 | Hansen et al. |
| 7,062,329 B2 | 6/2006 | Ostroff |
| 7,128,600 B2 | 10/2006 | Osypka |
| 7,130,699 B2 | 10/2006 | Huff et al. |
| 7,155,283 B2 | 12/2006 | Ries et al. |
| 7,191,009 B2 | 3/2007 | Laske et al. |
| 7,225,034 B2 | 5/2007 | Ries et al. |
| 7,228,177 B2 | 6/2007 | Receveur |
| 7,231,253 B2 | 6/2007 | Tidemand et al. |
| 7,241,180 B1 | 7/2007 | Rentas Torres |
| 7,244,150 B1 | 7/2007 | Brase et al. |
| 7,274,963 B2 | 9/2007 | Spadgenske |
| 7,283,878 B2 | 10/2007 | Brostrom et al. |
| 7,402,083 B2 | 7/2008 | Kast et al. |
| 7,548,788 B2 | 6/2009 | Chinn et al. |
| 7,761,165 B1 | 7/2010 | He et al. |
| 2003/0114905 A1 | 6/2003 | Kuzma |
| 2003/0120327 A1 | 6/2003 | Tobritzhofer et al. |
| 2003/0163171 A1 | 8/2003 | Kast et al. |
| 2003/0204215 A1 | 10/2003 | Gunderson et al. |
| 2004/0034392 A1 | 2/2004 | Spadgenske |
| 2004/0059392 A1 | 3/2004 | Parramon et al. |
| 2004/0064164 A1 | 4/2004 | Ries et al. |
| 2004/0068302 A1 | 4/2004 | Rodgers et al. |
| 2004/0072475 A1 | 4/2004 | Istvan |
| 2004/0093051 A1 | 5/2004 | Chinn et al. |
| 2004/0230267 A1 | 11/2004 | Wenger |
| 2004/0232597 A1 | 11/2004 | Sjostedt et al. |
| 2004/0267328 A1 | 12/2004 | Duffin et al. |
| 2005/0033371 A1 | 2/2005 | Sommer et al. |
| 2005/0043770 A1 | 2/2005 | Hine et al. |
| 2005/0043771 A1 | 2/2005 | Sommer et al. |
| 2005/0131483 A1 | 6/2005 | Zhao et al. |
| 2005/0165465 A1 | 7/2005 | Pianca et al. |
| 2006/0004420 A1 | 1/2006 | Rossing et al. |
| 2006/0009819 A1 | 1/2006 | Przybyszewski |
| 2006/0030224 A1 | 2/2006 | Degroot et al. |
| 2006/0041293 A1 | 2/2006 | Mehdizadeh et al. |
| 2006/0167522 A1 | 7/2006 | Malinowski |
| 2006/0172611 A1 | 8/2006 | Rodgers et al. |
| 2006/0241715 A1 | 10/2006 | Sprain et al. |
| 2006/0259106 A1 | 11/2006 | Arnholt et al. |
| 2007/0142888 A1 | 6/2007 | Chavez |
| 2007/0150007 A1 | 6/2007 | Anderson et al. |
| 2007/0150036 A1 | 6/2007 | Anderson |
| 2007/0161294 A1 | 7/2007 | Brase et al. |
| 2007/0202728 A1 | 8/2007 | Olson et al. |
| 2007/0219595 A1 | 9/2007 | He |
| 2007/0225772 A1 | 9/2007 | Lahti et al. |
| 2007/0239243 A1 | 10/2007 | Moffitt et al. |
| 2008/0015668 A1 | 1/2008 | Soukup |
| 2008/0039917 A1 | 2/2008 | Cross et al. |
| 2008/0071320 A1 | 3/2008 | Brase |
| 2008/0177167 A1 | 7/2008 | Janzig et al. |

FOREIGN PATENT DOCUMENTS

| | | |
|---|---|---|
| WO | 03075414 A1 | 9/2003 |
| WO | 2004033035 A2 | 4/2004 |

OTHER PUBLICATIONS

U.S. Appl. No. 12/210,600 Official Communication dated May 21, 2012.

LEAD CONNECTION SYSTEM FOR AN IMPLANTABLE ELECTRICAL STIMULATION SYSTEM AND METHODS FOR MAKING AND USING THE SYSTEMS

CROSS-REFERENCE TO RELATED APPLICATIONS

This patent application is a continuation of U.S. patent application Ser. No. 12/210,600 filed Sep. 15, 2008, which is incorporated herein by reference.

TECHNICAL FIELD

The present invention is directed to the area of implantable electrical stimulation systems and methods of making and using the implantable electrical stimulation systems. The present invention is also directed to a lead connection system for facilitating the trial stimulation of one or more electrodes on one or more implanted leads of an implantable electrical stimulation system, as well as methods of making and using the systems.

BACKGROUND

Implantable electrical stimulation systems have proven therapeutic in a variety of diseases and disorders. For example, spinal cord stimulation systems have been used as a therapeutic modality for the treatment of chronic pain syndromes. Deep brain stimulation has also been useful for treating refractory chronic pain syndromes and has been applied to treat movement disorders and epilepsy. Peripheral nerve stimulation has been used to treat chronic pain syndrome and incontinence, with a number of other applications under investigation. Functional electrical stimulation systems have been applied to restore some functionality to paralyzed extremities in spinal cord injury patients. Moreover, electrical stimulation systems can be implanted subcutaneously to stimulate subcutaneous tissue including subcutaneous nerves such as the occipital nerve.

Stimulators have been developed to provide therapy for a variety of treatments. A stimulator can include a control module (with a pulse generator), one or more leads, and an array of stimulator electrodes on each lead. The stimulator electrodes are in contact with or near the nerves, muscles, or other tissue to be stimulated. The pulse generator in the control module generates electrical pulses that are delivered by the electrodes to body tissue.

BRIEF SUMMARY

In one embodiment, a lead connection system includes a connector housing, a plurality of lead retainers disposed on the connector housing, a plurality of connector contacts, and a single connector cable. The connector housing is configured and arranged to receive a proximal end of each of a plurality of leads. Each of the plurality of leads has a plurality of terminals disposed on the proximal end. The plurality of lead retainers are disposed in the connector housing. Each lead retainer is configured and arranged to removably attach the proximal end of one of the received plurality of leads to the connector housing. The plurality of lead retainers include at least one of a slidable drawer and at least one pivotable hinged panel. The plurality of connector contacts are configured and arranged for making electrical contact with one or more of the terminals of one or more of the plurality of received leads. The single connector cable has a proximal end and a distal end. The distal end is electrically coupled to the plurality of connector contacts and the proximal end is configured and arranged for insertion into a trial stimulator. The cable connector is electrically coupled, via the connector contacts, to at least one terminal of each of the received plurality of leads.

In another embodiment, an electrical-stimulator testing system includes a plurality of leads, a connector housing configured and arranged to receive a proximal end of each of the plurality of leads, a plurality of lead retainers disposed in the connector housing, a plurality of connector contacts, a single connector cable, and a trial stimulator. Each lead includes a plurality of electrodes disposed on a distal end of the lead, a plurality of terminals disposed on the proximal end of the lead, and a plurality of conductor wires extending along the lead to couple the electrodes electrically to the terminals. Each lead retainer is configured and arranged to removably attach the proximal end of one of the received plurality of leads to the connector housing. The plurality of lead retainers includes at least one of a slidable drawer and at least one pivotable hinged panel. A plurality of connector contacts are disposed in the connector housing and configured and arranged for making electrical contact with one or more of the plurality of terminals of the plurality of received leads. The single connector cable has a proximal end and a distal end. The distal end is electrically coupled to the plurality of connector contacts. The cable connector is electrically coupled, via the connector contacts, to at least one of the plurality of lead terminals of each of the received at least one of the leads. The trial stimulator is electrically coupleable to the proximal end of the connector cable. The trial stimulator is configured and arranged for providing electrical signals to the electrodes on the plurality of leads.

In yet another embodiment, a method for stimulating patient tissue includes implanting at least a distal end of a plurality of leads into a patient. Each of the plurality of leads includes a plurality of electrodes disposed on the distal end of the leads and at least one terminal disposed on a proximal end of the lead. The electrodes are electrically coupled to the at least one terminal. At least two proximal ends of the plurality of leads are disposed into a lead connection system that includes a plurality of lead retainers and a single connector cable with a distal end and a proximal end. Each lead retainer is configured and arranged to receive the proximal end of one of the plurality of leads and electrically couple the received lead to the distal end of the single connector cable. Each lead retainer includes at least one of a slidable drawer and at least one pivotable hinged panel. The proximal end of the connector cable is inserted into a trial stimulator. Electrical signals are provided from the trial stimulator to the electrodes on the plurality of leads.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The present invention is directed to the area of implantable electrical stimulation systems and methods of making and using the implantable electrical stimulation systems. The present invention is also directed to a lead connection system for facilitating the trial stimulation of one or more electrodes on one or more implanted leads of an implantable electrical stimulation system, as well as methods of making and using the systems.

Suitable implantable electrical stimulation systems include, but are not limited to, an electrode lead ("lead") with one or more electrodes disposed on a distal end of the lead and one or more contact terminals disposed on a proximal end of the lead. Leads include, for example, percutaneous leads, paddle leads, and cuff leads. Examples of electrical stimulation systems with leads are found in, for example, U.S. Pat. Nos. 6,181,969; 6,516,227; 6,609,029; 6,609,032; and 6,741,892; and U.S. patent application Ser. Nos. 10/353,101, 10/503,281, 11/238,240; 11/319,291; 11/327,880; 11/375,638; 11/393,991; and 11/396,309, all of which are incorporated by reference.

Figure 1:
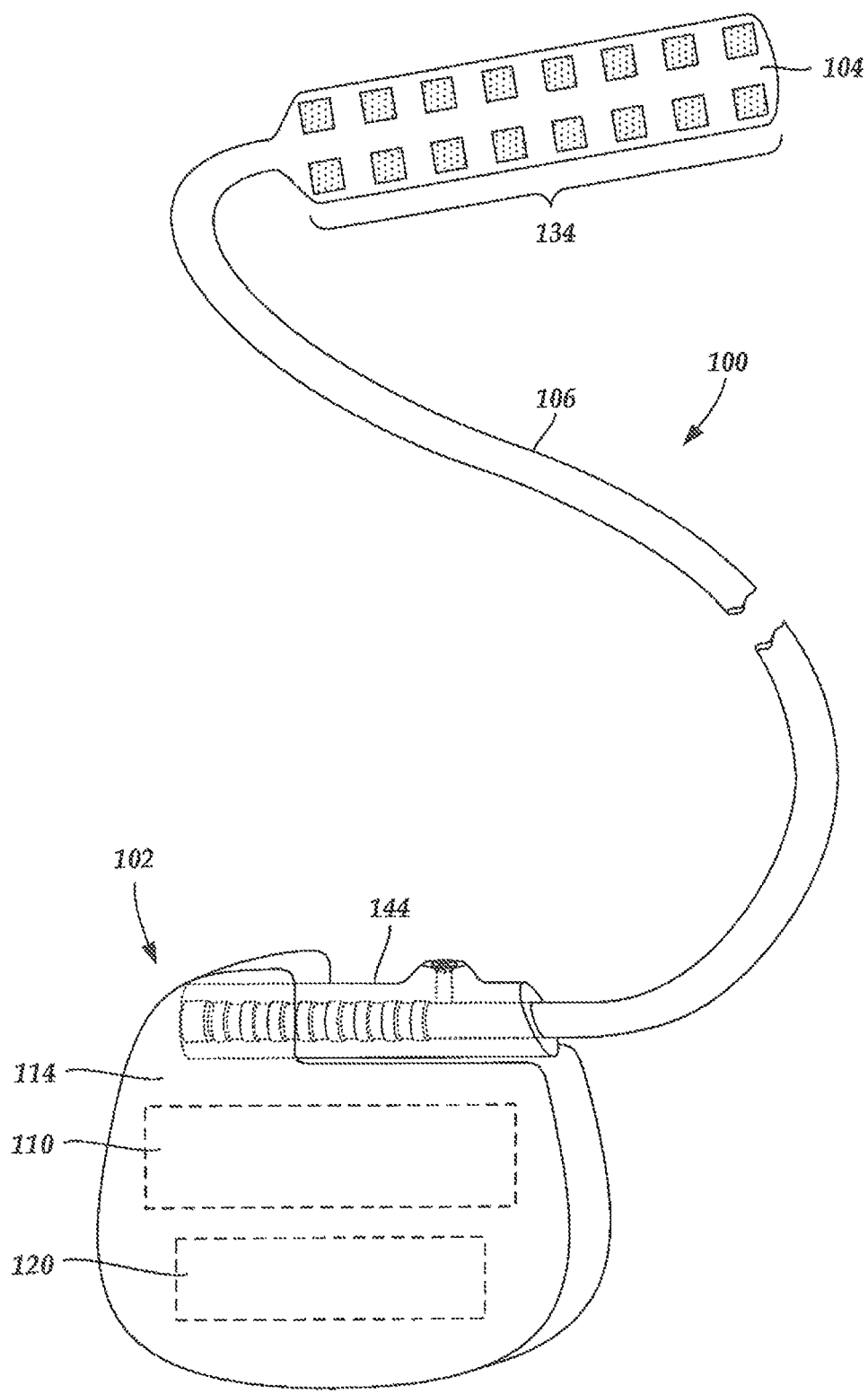
FIG. 1 is a schematic view of one embodiment of an electrical stimulation system, according to the invention.
Figure 2:
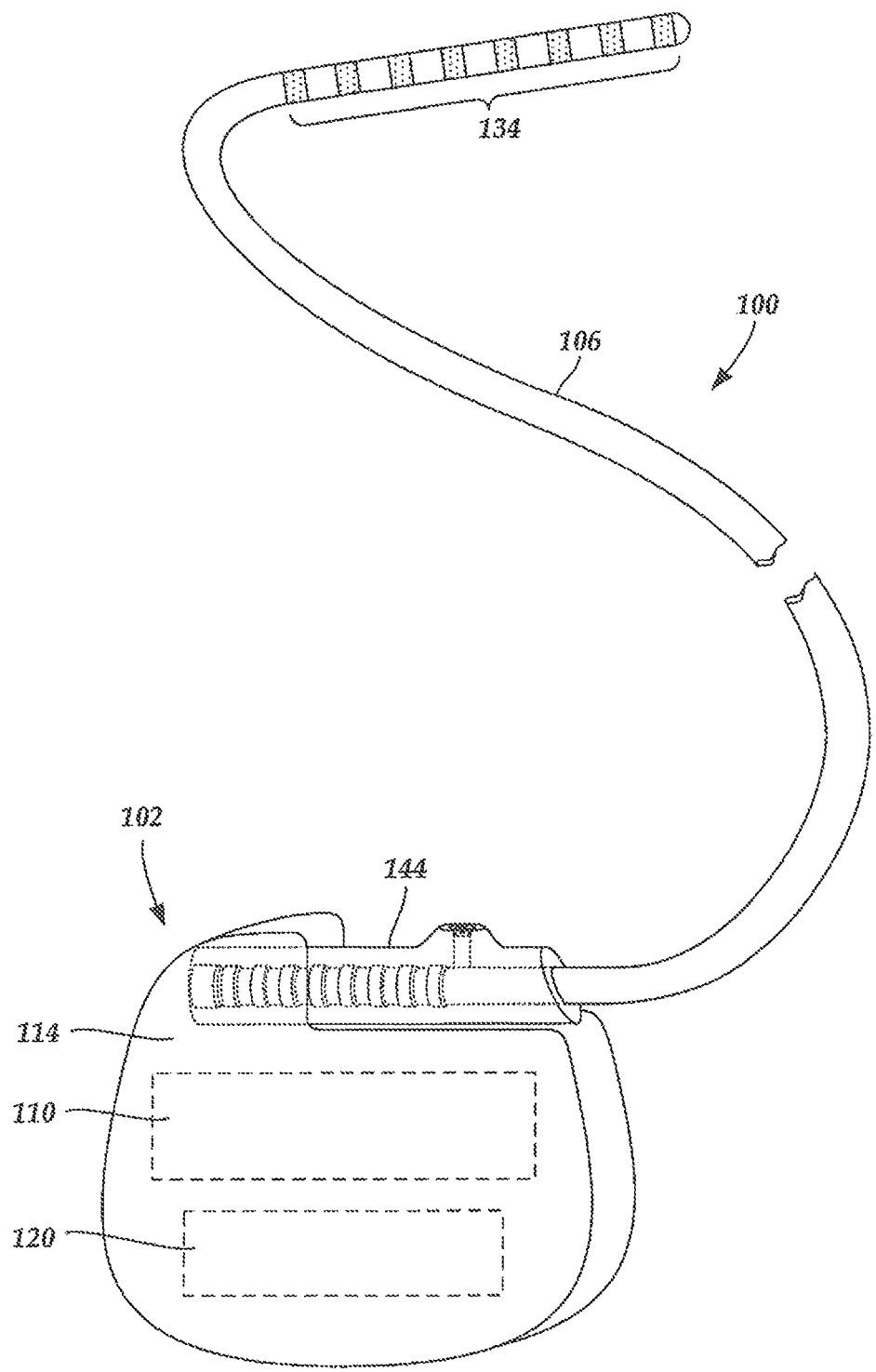
FIG. 2 is a schematic view of another embodiment of an electrical stimulation system, according to the invention.

FIG. 1 illustrates schematically one embodiment of an electrical stimulation system 100. The electrical stimulation system includes a control module (e.g., a stimulator or pulse generator) 102, a paddle body 104, and at least one lead body 106 coupling the control module 102 to the paddle body 104. The paddle body 104 and the lead body 106 form a lead. The paddle body 104 typically includes an array of electrodes 134. The control module 102 typically includes an electronic subassembly 110 and an optional power source 120 disposed in a sealed housing 114. The control module 102 typically includes a connector receptacle 144 (see FIGS. 2, and 3A-3B) into which the proximal end of the lead body 106 can be plugged to make an electrical connection via conductive contacts on the control module 102 and contact terminals on the lead body 106. It will be understood that the electrical stimulation system can include more, fewer, or different components and can have a variety of different configurations including those configurations disclosed in the electrical stimulation system references cited herein. For example, instead of a paddle body 104, the electrodes 134 can be disposed in an array at or near the distal end of the lead body 106 forming a percutaneous lead, as illustrated in FIG. 2. A percutaneous lead may be isodiametric along the length of the lead. In addition, one or more lead extensions 312 (see FIG. 3B) can be disposed between the lead body 106 and the control module 102 to extend the distance between the lead body 106 and the control module 102 of the embodiments shown in FIGS. 1 and 2.

The electrical stimulation system or components of the electrical stimulation system, including one or more of the lead body 106, the paddle body 104, and the control module 102, are typically implanted into the body of a patient. The electrical stimulation system can be used for a variety of applications including, but not limited to, brain stimulation, neural stimulation, spinal cord stimulation, muscle stimulation, and the like.

The electrodes 134 can be formed using any conductive, biocompatible material. Examples of suitable materials include metals, alloys, conductive polymers, conductive carbon, and the like, as well as combinations thereof. The number of electrodes 134 in the array of electrodes 134 may vary. For example, there can be two, four, six, eight, ten, twelve, fourteen, sixteen, or more electrodes 134. As will be recognized, other numbers of electrodes 134 may also be used.

The electrodes of the paddle body 104 or lead body 106 are typically disposed in, or separated by, a non-conductive, biocompatible material including, for example, silicone, polyurethane, polyetheretherketone ("PEEK"), epoxy, and the like or combinations thereof. The paddle body 104 and lead body 106 may be formed in the desired shape by any process including, for example, molding (including injection molding), casting, and the like. Electrodes and connecting wires can be disposed onto or within a paddle body either prior to or subsequent to a molding or casting process. The non-conductive material typically extends from the distal end of the lead to the proximal end. The non-conductive, biocompatible material of the paddle body 104 and the lead body 106 may be the same or different. The paddle body 104 and the lead body 106 may be a unitary structure or can be formed as two separate structures that are permanently or detachably coupled together.

Terminals (not shown) are typically disposed at the proximal end of the lead for connection to corresponding conductive contacts (not shown) in the control module 102 (or to conductive contacts on a lead extension). Conductor wires (not shown) extend from the terminals (not shown) to the electrodes 134. Typically, one or more electrodes 134 are electrically coupled to a terminal (not shown). In some embodiments, each terminal (not shown) is only connected to one electrode 134. The conductor wires may be embedded in the non-conductive material of the lead or can be disposed in one or more lumens 506 (e.g., lumen 506 of FIG. 5A) extending along the lead. In some embodiments, there is an individual lumen for each conductor wire. In other embodiments, two or more conductor wires may extend through a lumen. There may also be one or more lumens (e.g., lumen 504 of FIG. 5A) that open at, or near, the proximal end of the lead, for example, for inserting a stylet rod to facilitate placement of the lead within a body of a patient. Additionally, there may also be one or more lumens that open at, or near, the distal end of the lead, for example, for infusion of drugs or medication into the site of implantation of the paddle body 104.

During implantation of the lead into a patient, it is sometimes desirable to test the positioning or functionality of the electrodes within the patient prior to the completion of the implantation. One way to test electrode positioning or functionality is to implant an electrode-including distal end of a lead (and, optionally, one or more lead extensions) into the patient. The proximal end of the lead (or lead extension) can then be electrically coupled to a trial stimulator to perform one or more trial stimulations using the electrodes. Once it is determined that the electrodes are properly positioned and functioning within desired parameters, the trial stimulator can be removed from the proximal end of the lead (or lead extension) and replaced with a control module and the implantation can be completed.

The lead can be electrically coupled to the trial stimulator by electrically coupling the proximal end of the lead (or lead extension) to a distal end of a cable that is, in turn, electrically coupled to the trial stimulator. Attachment of the lead (or lead extension) to the cable can sometimes be time-consuming or labor-intensive. Additionally, when multiple leads are implanted into a patient, a medical practitioner sometimes needs to separately attach each lead (or lead extension) to a separate cable.

A stylet is sometimes used by medical practitioners to facilitate the guidance of the distal end of the lead to a desired position within the patient. The stylet is sometimes inserted into the lead through the proximal end of the lead. When the stylet is inserted into the proximal end of the lead, the stylet may interfere with subsequent attachment of the lead to the trial stimulator. However, it is sometimes desirable to retain the stylet within the lead during trial stimulation in order to facilitate further adjustment of the positioning of the lead during, or subsequent to, the trial stimulation.

Figure 3:
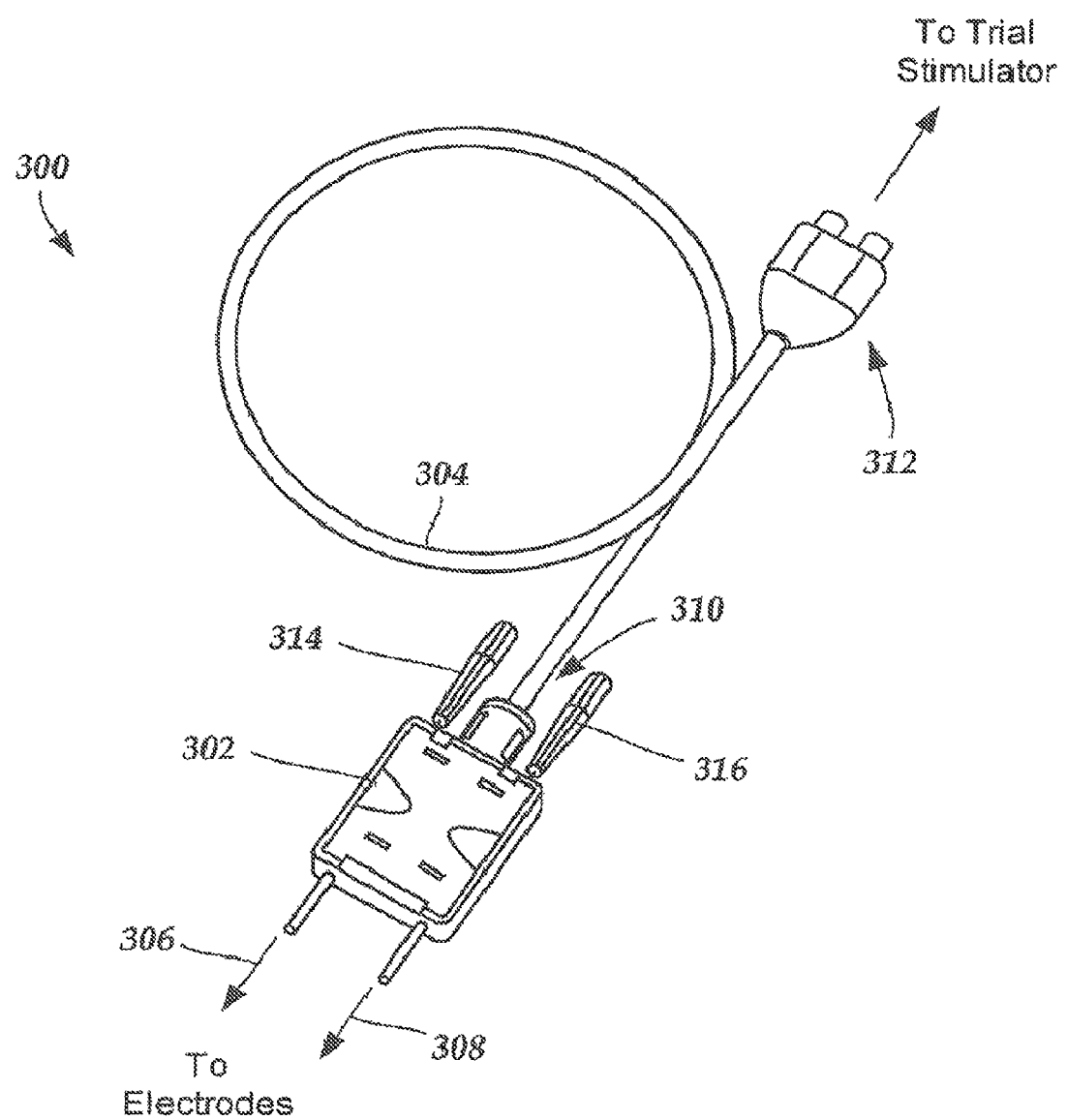
FIG. 3 is a schematic perspective view of one embodiment of portions of two leads in a lead connection system, according to the invention.

FIG. 3 is a schematic perspective view of one embodiment of a lead connection system 300 for coupling one or more leads to a trial stimulator or other stimulator. The lead connection system 300 includes a connector housing 302 and a connector cable 304. In FIG. 3, two leads 306 and 308 are shown retained in the connector housing 302. The connector cable 304 includes a distal end 310 that is electrically coupled to a proximal end 312. The retained leads 306 and 308 can be electrically coupled to the distal end 310 of the connector cable 304. The proximal end 312 of the connector cable 304 can be configured and arranged to attach to a trial stimulator.

In at least some embodiments, stylets 314 and 316 can be inserted into the leads 306 and 308, respectively, and used to guide the leads 306 and 308 before, or while, the leads 306 and 308 are retained in the connector housing 302. A connector housing can be formed using many different non-conductive, rigid materials including, for example, plastic, polypropylene, and the like or combinations thereof. The connector housing may be formed in the desired shape by any process including, for example, molding (including injection molding), casting, and the like.

Figure 4:
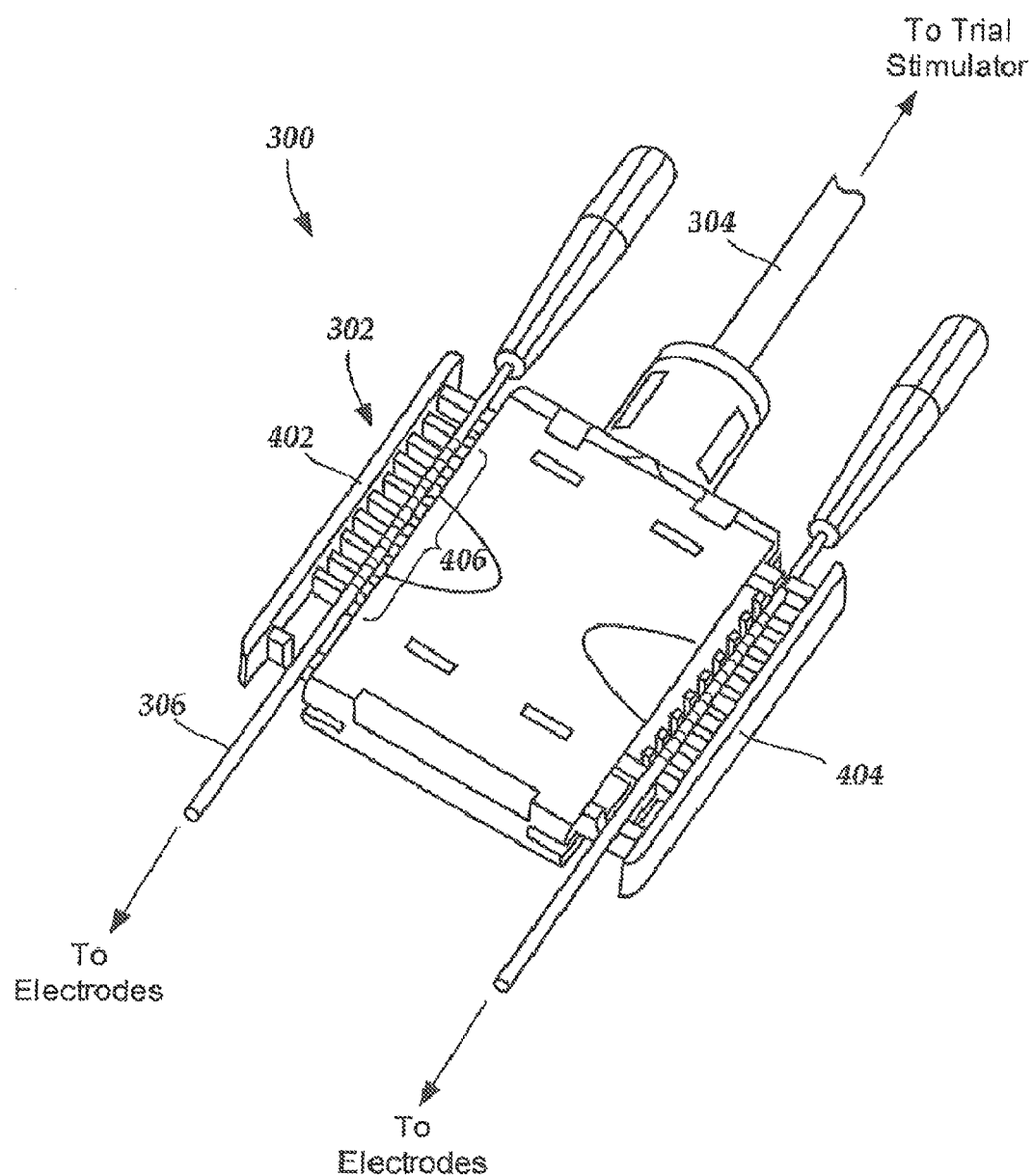
FIG. 4 is a schematic perspective view of one embodiment of a connector housing with two leads placed in two open drawers of a lead connection system, according to the invention.

The connector housing includes one or more lead retainers for retaining one or more leads and for electrically coupling the one or more retained leads to the connector cable. In at least some embodiments, the connector housing uses one or more drawers to retain the lead(s). FIG. 4 is a schematic perspective view of the connector housing 302 with two drawers 402 and 404 shown in an open position. Leads can be placed in one or more of the drawers 402 and 404 while the one or more drawers 402 and 404 are in an open position and each of the lead-containing drawers 402 and 404 can subsequently be slid to a closed position, or otherwise closed, to retain the one or more received leads within the connector housing. For example, in FIG. 4 the lead 306 has been placed in the open drawer 402. The drawer 402 can subsequently be slid to a closed position (e.g., FIG. 3 and FIG. 7) to retain the lead 314. Any number of drawers 402 and 404 can be disposed in a connector housing 302. For example, there can be one, two, three, four, six, eight, ten, or more drawers 402 and 404. As will be recognized, other numbers of drawers 402 and 404 may also be used.

When the lead 306 is retained in the connector housing 302, terminals on the lead 306 are aligned with connector contacts in the connector housing 302 that are electrically coupled to the connector cable 304. For example, when the lead 306 is placed in the open drawer 402 and the drawer 402 is slid to a closed position, or otherwise closed, terminals 406 on the lead 306 are aligned with one or more connector contacts (e.g. connector contact 506 of FIG. 5) in the connector housing 302. The connector contacts are electrically coupled to the connector cable 304. The connector cable 304 is configured and arranged for electrically coupling to a trial stimulator, or other stimulator. Thus, the lead connection system 300 can be used to electrically couple electrodes on the lead 306 to a trial stimulator.

Figure 5:
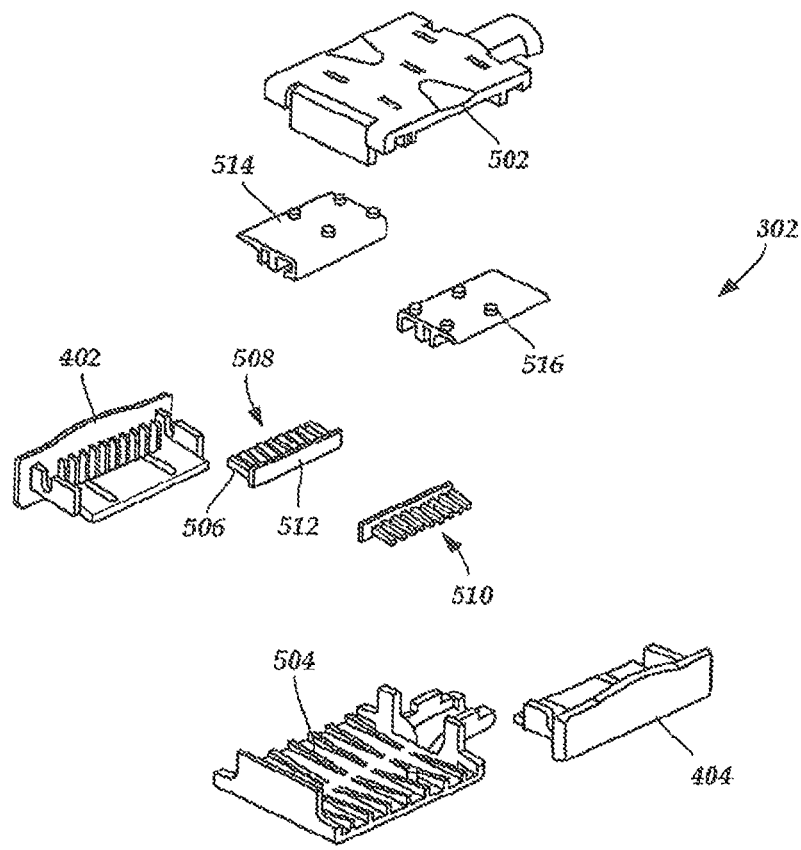
FIG. 5 is a schematic exploded perspective view of one embodiment of a portion of a lead connection system, according to the invention.

FIG. 5 is a schematic exploded perspective view of one embodiment of the connector housing 302. In the illustrated embodiment, the connector housing 302 includes a first body portion 502, a second body portion 504, the drawers 402 and 404, and a plurality of connector contacts, such as connector contact 506. In at least some embodiments, a plurality of connector contacts are coupled together as one or more contact elements. For example, in FIG. 5 connective contacts are coupled together into two contact elements 508 and 510. Any number of contact elements can be used. For example, there can be one, two, three, four, six, eight, ten, or more contact elements. As will be recognized, other numbers of contact elements may also be used.

In at least some embodiments, the number of contact elements corresponds to the number of lead retainers disposed in the connector housing. For example, in FIG. 5 the connector housing 302 includes two drawers 402 and 404 and two corresponding contact elements 508 and 510, respectively.

Any number of connector contacts can be included within each contact element. For example, there can be two, four, six, eight, ten, twelve, fourteen, sixteen, or more connector contacts within each contact element. As will be recognized, other numbers of connector contacts within a contact element may also be used. In at least some embodiments, the number of connector contacts in each contact element corresponds to the number of terminals on a retained lead. For example, referring to both FIG. 4 and FIG. 5, the contact element 508 can be configured and arranged to align each connector contact to one of the terminals 406 of the lead 306 retained in the connector housing 302. Connector contacts can be formed using any conductive material. Examples of suitable materials include metals, alloys, conductive polymers, conductive carbon, and the like, as well as combinations thereof. In at least some embodiments, the connector contacts are connector pins configured and arranged to correspond in number, shape, size, and alignment to terminals disposed on a lead retained by a lead retainer.

In at least some embodiments, the connector contacts are electrically coupled to the connector cable 304 by a plurality of connector wires (not shown), or using one or more printed circuit boards, or any other suitable arrangement for electrically coupling. As an example, in FIG. 5 a printed circuit board 512 is shown attached to the contact element 508. In at least some embodiments, the contact elements 508 and 510 and corresponding printed circuit boards are attached to the connector housing 302 via connector-contact holders. For example, in FIG. 5, connector-contact holder 514 can be used to hold contact element 508 in position and a connector-contact holder 516 can be used to hold contact element 510 in position. In at least some embodiments, the contact elements are configured and arranged to retain a plurality of connector wires (not shown) electrically coupling the one or more printed circuit boards to the connector cable 304.

Figure 6:
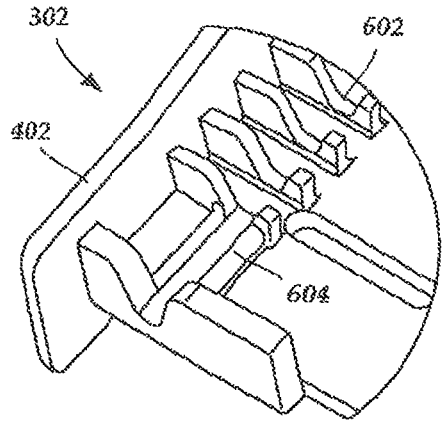
FIG. 6 is a schematic close-up perspective view of a portion of one embodiment of a drawer of a connector housing of a lead connection system, according to the invention.

In at least some embodiments, a lead placed in an open drawer can be placed on one or more lead-retention members disposed on the drawer which, upon sliding the drawer to a closed position, sandwich the lead between the one or more lead-retention members of the drawer and one or more lead-retention members disposed on an inner surface of the first body portion of the connector housing. FIG. 6 is a schematic close-up perspective view of a portion of the drawer 402 of the connector housing 302. In FIG. 6, the drawer 402 includes a plurality of lead-retention members, such as lead-retention member 602. Additionally, drawers may include one or more lead saddles between one or more lead-retention members. For example, in FIG. 6 the drawer 402 includes a lead saddle 604. The number of lead-retention members and lead saddles disposed in a drawer may vary. The lead-retention members and lead saddles can be formed from many different materials and disposed in a drawer in many different ways.

Figure 7:
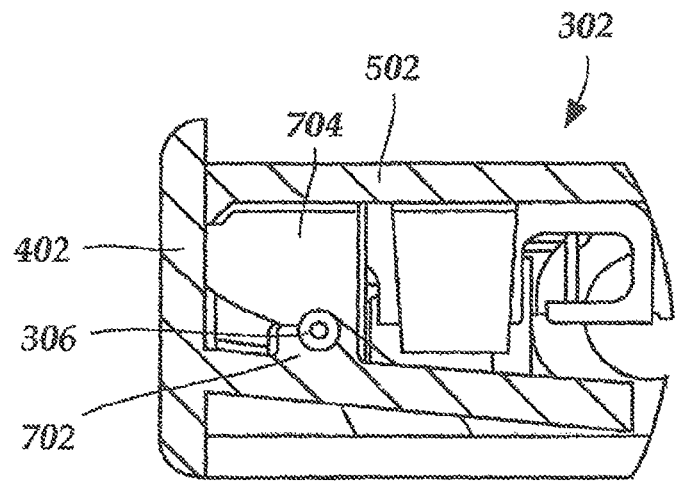
FIG. 7 is a schematic transverse cross-sectional view of one embodiment of a lead retained in a portion of a lead connection system, according to the invention.

For example, in one embodiment lead-retention members and lead saddles are formed from plastic and molded integrally with the drawers and connector housing. A lead can be retained in a connector housing by placing the lead in an open drawer and sliding the drawer to a closed position. FIG. 7 is a schematic transverse cross-sectional view of the lead 306 retained in a portion of the connector housing 302 between the closed drawer 402 and an inner surface of the first body portion 502 of the connector housing 302. In FIG. 7, the lead 306 is shown sandwiched between a lead-retention member 702 attached to the drawer 402 and a lead-retention member 704 disposed on the inner surface of the first body portion 502.

Figure 8:
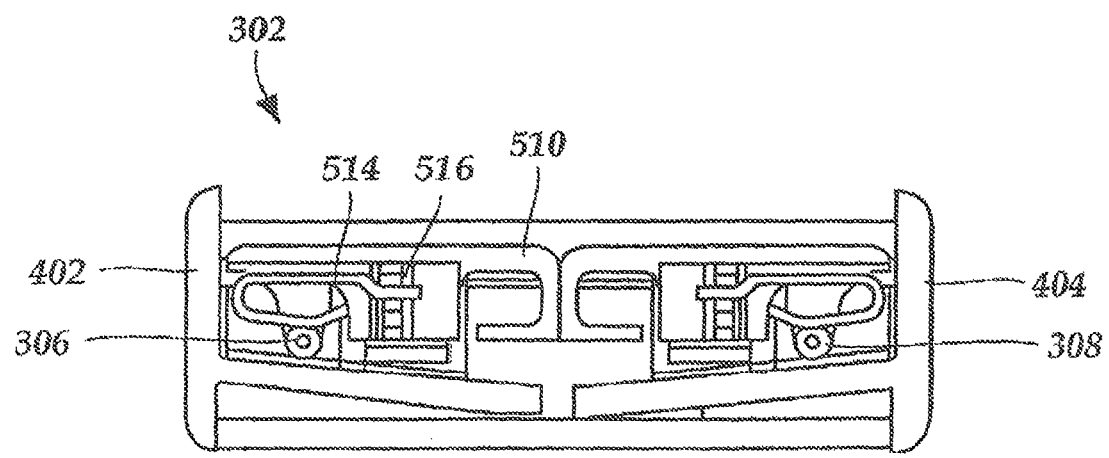
FIG. 8 is a schematic transverse cross-sectional view of one embodiment of two retained leads in a lead connection system contacting connector contacts, according to the invention.

A retained lead can be electrically coupled to one or more contact elements. FIG. 8 is a schematic transverse cross-sectional view of leads 306 and 308 retained in the connector housing 302. In FIG. 8, the lead 306 is shown retained in the drawer 402. A terminal (not shown) on the lead 306 is contacting the conductor contact 514. The conductor contact 514 is attached to the connector housing 302, via connector-contact holder 510. The conductor contact 514 is electrically coupled to the printed circuit board 516, which, in turn is electrically coupled to the connector cable 304 (not shown). The lead 308 is shown similarly retained in the drawer 404 of the connector housing 302.

In at least some embodiments, a removable attachment mechanism can be used to maintain a drawer in a closed position until a predetermined amount of force is applied to slide the drawer to an open position. In some embodiments, one or more cantilever snap-fit bosses are positioned on an inner surface of a drawer that mate with one or more corresponding undercut notches disposed on an inner surface of a connector housing. In other embodiments, the one or more cantilever snap-fit bosses are disposed on the inner surface of the connector housing and the corresponding one or more undercut notches are disposed on the inner surface of the drawer. In at least some embodiments, one or more of the drawers 402 and 404 are spring loaded. In at least some embodiments, one or more of the drawers 402 and 404 spring from a closed position to an open position when transitioned from a locked to an unlocked state.

Figure 9:
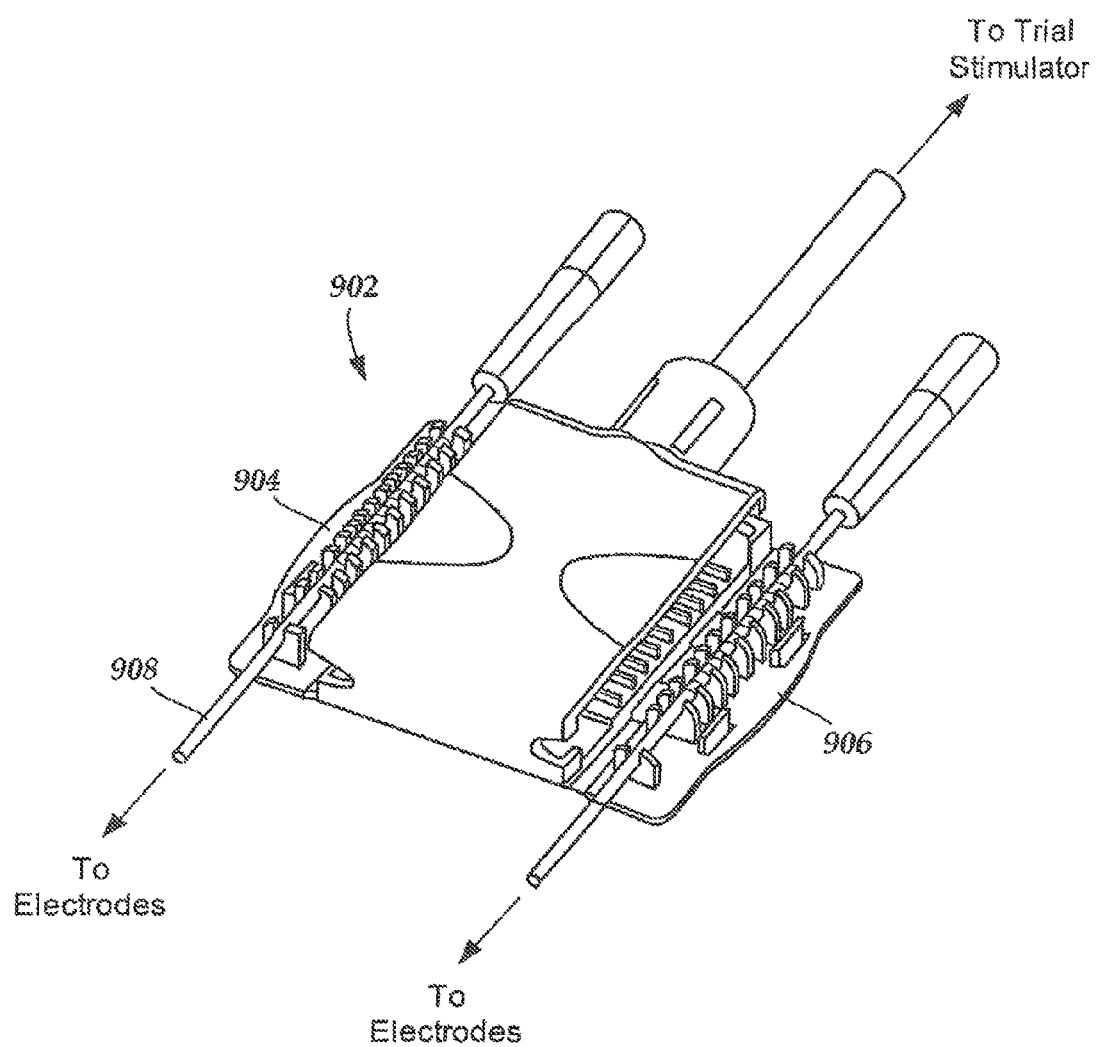
FIG. 9 is a schematic perspective view of a second embodiment of a lead connection system with two leads placed in two open hinged panels, according to the invention.

As discussed above, a connector housing can include one or more lead retainers for retaining one or more leads and for electrically coupling the one or more retained leads to a connector cable. In at least some embodiments, the connector housing uses one or more hinged panels to retain one or more leads. FIG. 9 is a schematic perspective view of a connector housing 902 with two hinged panels 904 and 906 shown in an open position. Leads can be placed in one or more of the hinged panels 904 and 906 while the one or more hinged panels 904 and 906 are in an open position and each of the lead-containing hinged panels 904 and 906 can be pivoted to a closed position to retain the received lead. For example, in FIG. 9, the lead 908 is shown placed in the open hinged panel 904. The hinged panel 904 can subsequently be pivoted to a closed position (e.g., FIG. 3 and FIG. 11) to retain the lead 908 and make electrical contact can between the terminals on the lead 908 and one or more connector contacts in the connector housing 902. Any number of hinged panels 904 and 906 disposed in a connector housing 902 can be used. For example, there can be one, two, three, four, six, eight, ten, or more hinged panels 904. As will be recognized, other numbers of hinged panels 904 and 906 may also be used.

Figure 10:
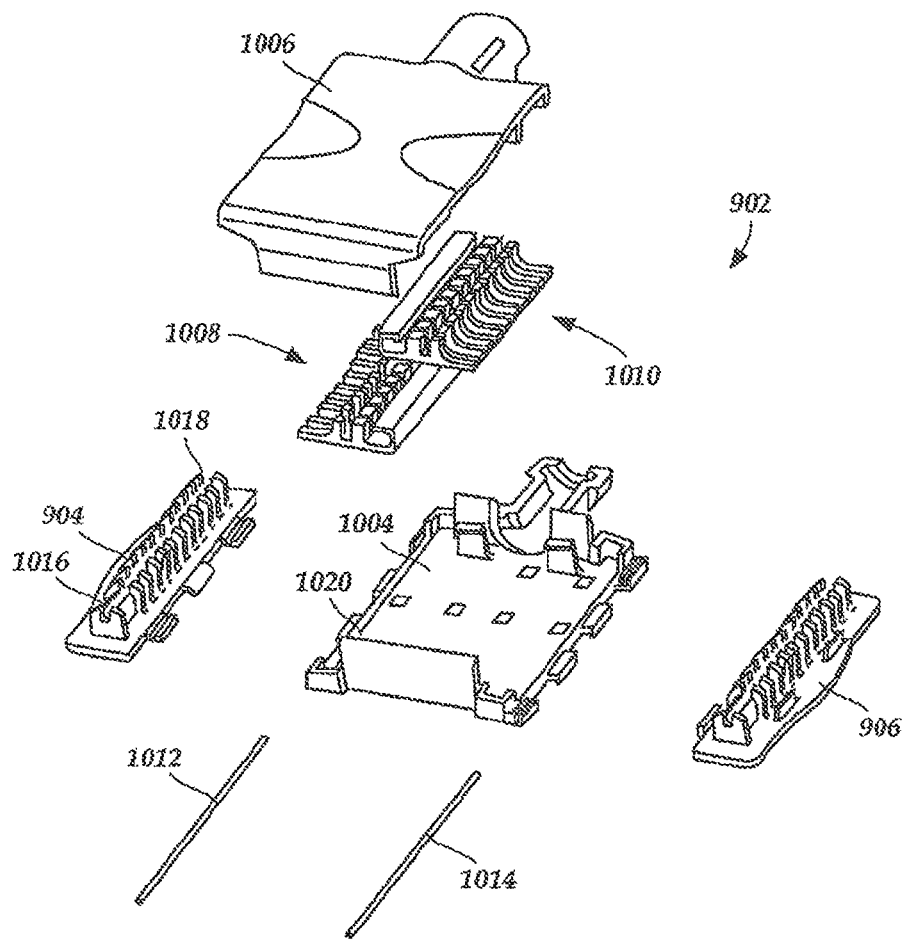
FIG. 10 is a schematic exploded perspective view of a second embodiment of a lead connection system, according to the invention.

FIG. 10 is a schematic exploded perspective view of one embodiment of the connector housing 902. The connector housing 902 includes a first body portion 1004, a second body portion 1006, the hinged panels 904 and 906, contact elements 1008 and 1010, and hinged-panel pins 1012 and 1014. In at least some embodiments, the hinge panels 904 and 906 retain leads in a manner similar to drawers by closing to sandwich a lead between a plurality of lead-retention members (and, optionally, one or more lead saddles) disposed on the hinged-panels and the first body portion 1004. For example, the hinged panels 904 and 906 each contain a lead saddle, such as the lead saddle 1016, and a plurality of lead-retention members, such as lead-retention member 1018. Additionally, the connector housing 902 contains one or more lead-retention members, such as lead-retention member 1020 disposed on an inner surface of the first body portion 1004. In at least some embodiments, pins are used to couple hinged panels to a connector housing. For example, in FIG. 10 hinged-panel pins 1012 and 1014 can be used to couple hinged panels 904 and 906, respectively, to the first body portion 1004. In other embodiments, a hinge with no moving parts, such as a living hinge, is used. Typically living hinges utilize a thin, bendable piece of material in lieu of one or more hinged-panel pins. In embodiments where a living hinge is used, a first body portion, a second body portion, and hinged panels can be formed as a unitary structure.

Figure 11A:
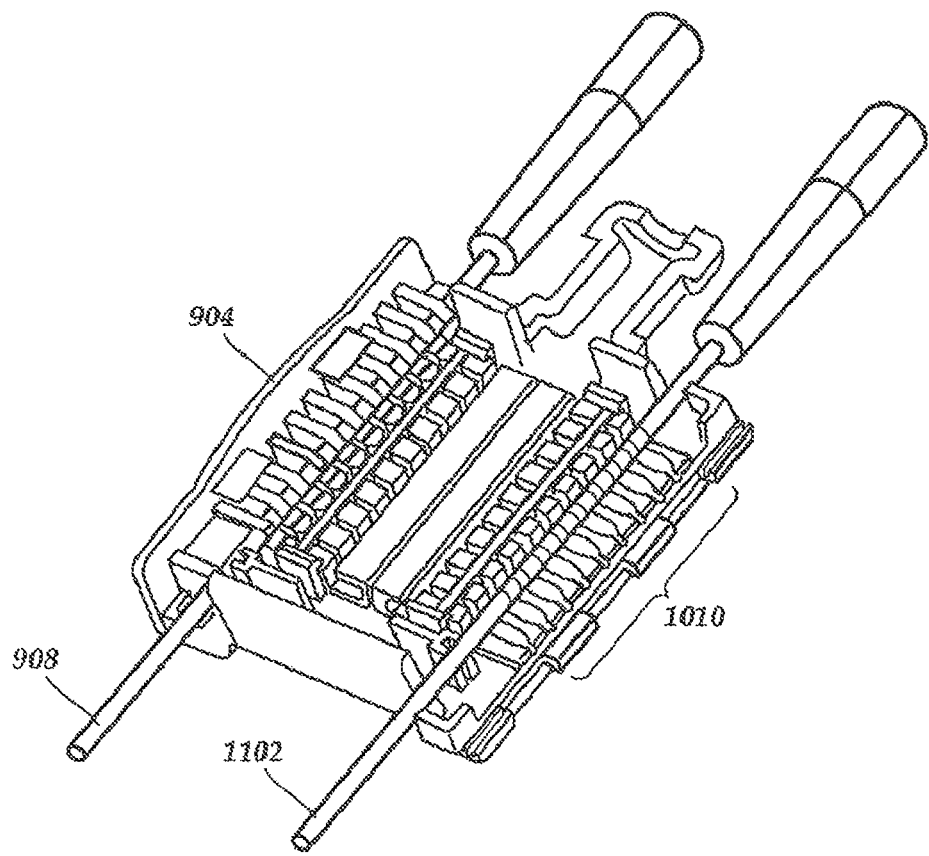
FIG. 11A is a schematic perspective view of a second embodiment of the lead connection system omitting a second body portion and a hinged panel, according to the invention.
Figure 11B:
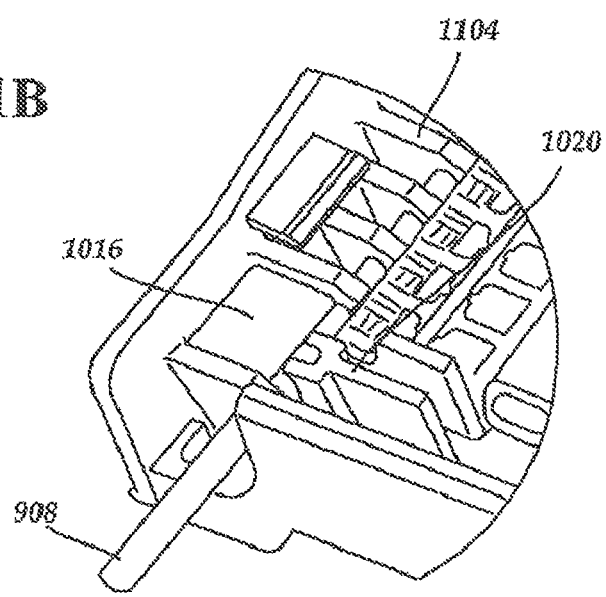
FIG. 11B is a schematic close-up perspective view of a lead retained in a portion of one embodiment of a lead connection system, according to the invention.

FIG. 11A is a schematic perspective view of the connector housing 902 omitting the second body portion 1006 and the hinged panel 906 for clarity of illustration. In FIG. 11A, the hinged panel 904 has been pivoted to a closed position to retain the lead 908, as shown in more detail in FIG. 11B. The second lead 1102 is positioned against the contact element 1010 to electrically couple terminals on the lead 1102 to connector contacts of the contact element 1010. FIG. 11B is a schematic close-up perspective view of the lead 908 retained by a portion of the hinged panel 904. In FIG. 11B, the lead 908 is shown sandwiched between the lead saddle 1016 and the plurality of lead-retention members of the hinged panel 904, such as lead-retention member 1104, and one or more lead-retention members, such as lead-retention member 1020, disposed on the first body portion 1004 of the connector housing 902.

Figure 12:
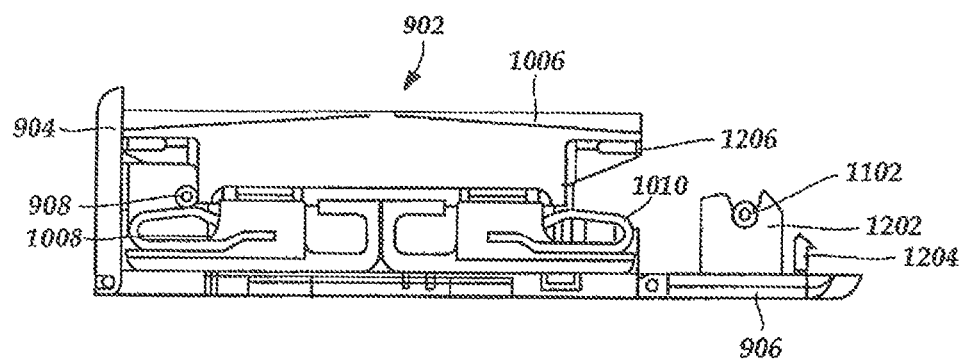
FIG. 12 is a schematic transverse cross-sectional view of a second embodiment of a lead connection system with one open hinged panel and one closed hinged panel, according to the invention.

FIG. 12 is a schematic transverse cross-sectional view of the connector housing 902 with the hinged panel 904 in a closed position and the hinged panel 906 in an open position. In FIG. 12, the lead 908 is retained in the connector housing 902 and electrically coupled to a connector contact of the contact element 1008. The lead 1102 has been positioned on the lead-retention member 1202 on the hinged panel 906. However, because the hinged panel 906 is in an open position, the lead 1102 is not electrically coupled to the connector contact 1010.

In at least some embodiments, a removable attachment mechanism can be used to maintain a hinged panel in a closed position until a predetermined amount of force is applied to pivot the hinged to an open position. In at least one embodiment, one or more cantilever snap-fit bosses, such as cantilever snap-fit boss 1204, are positioned on an inner surface of a hinged panel that mate with one or more corresponding undercut notches, such as undercut notch 1206, disposed on an inner surface of the second body portion 1006 of the connector housing 902. In alternate embodiments, the one or more cantilever snap-fit bosses are positioned on the inner surface of the second body portion and the corresponding one or more undercut notches are disposed on the inner surface of the hinged panel.

Figure 13:
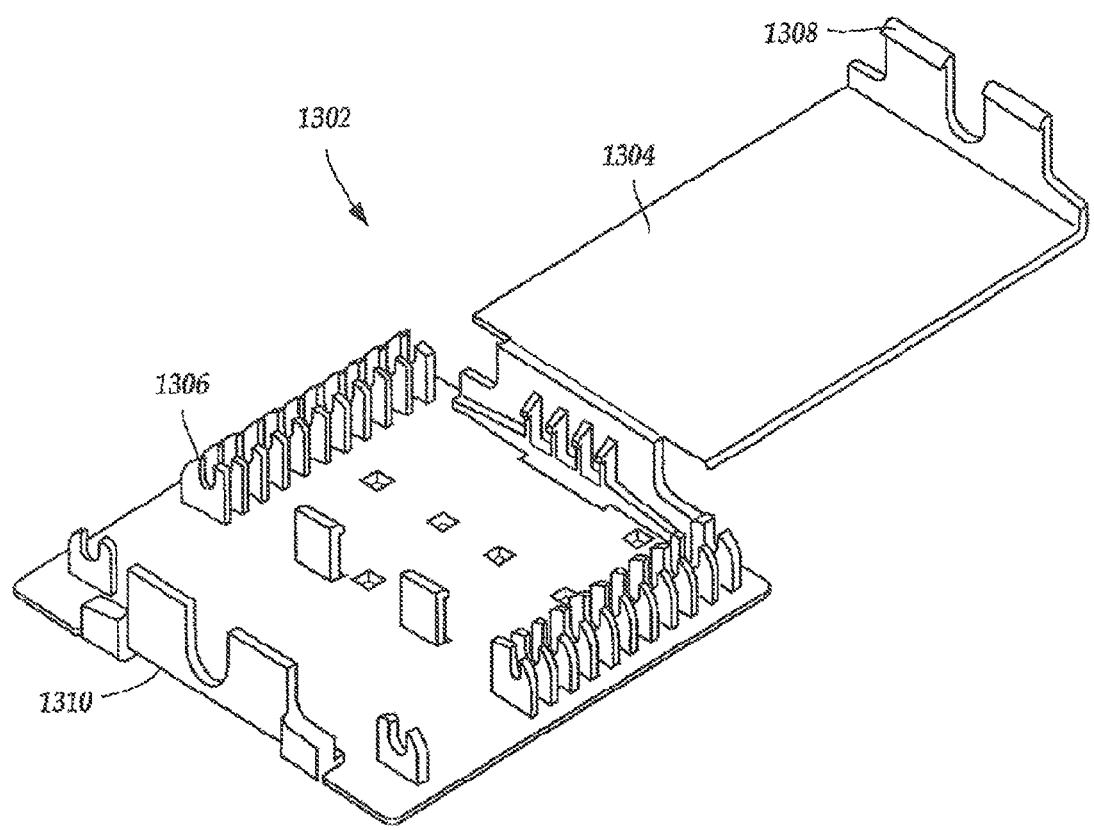
FIG. 13 is a schematic perspective view of a third embodiment of a lead connection system having a single living hinge, according to the invention.

In at least some embodiments, a connector housing includes a single hinged panel. FIG. 13 is a schematic perspective view of a connector housing 1302 with a single hinged panel 1304. In FIG. 13, the connector housing 1302 includes a plurality of lead-retention members, such as lead-retention member 1306, configured and arranged for the positioning of one or two leads when the hinged panel 1304 is open. When the hinged panel 1304 is closed, the retained one or two leads are sandwiched between a plurality of lead-retention members and an inner surface of the hinged panel 1304. In at least some embodiments, the hinged panel includes one or more cantilever snap-fit bosses, such as cantilever snap-fit boss 1308 positioned on the hinged panel 1304, that mate with one or more corresponding undercut notches, such as undercut notch 1310, disposed on the connector housing 1302. In alternate embodiments, the one or more cantilever snap-fit bosses are positioned on the connector housing and the corresponding one or more undercut notches are disposed on the hinged panel 1304. In at least some embodiments, pins are used to couple the hinged panel 1304 to the connector housing 1302. In other embodiments, a living hinge is used and the connector housing 1302 and hinged panel 1304 are formed as a unitary structure. Note that, in FIG. 13 the connector contacts are omitted for clarity of illustration. It may be an advantage to form the connector housing 1302 as a unitary structure to simplify the manufacturing process and, thereby, reduce cost.

Figure 14:
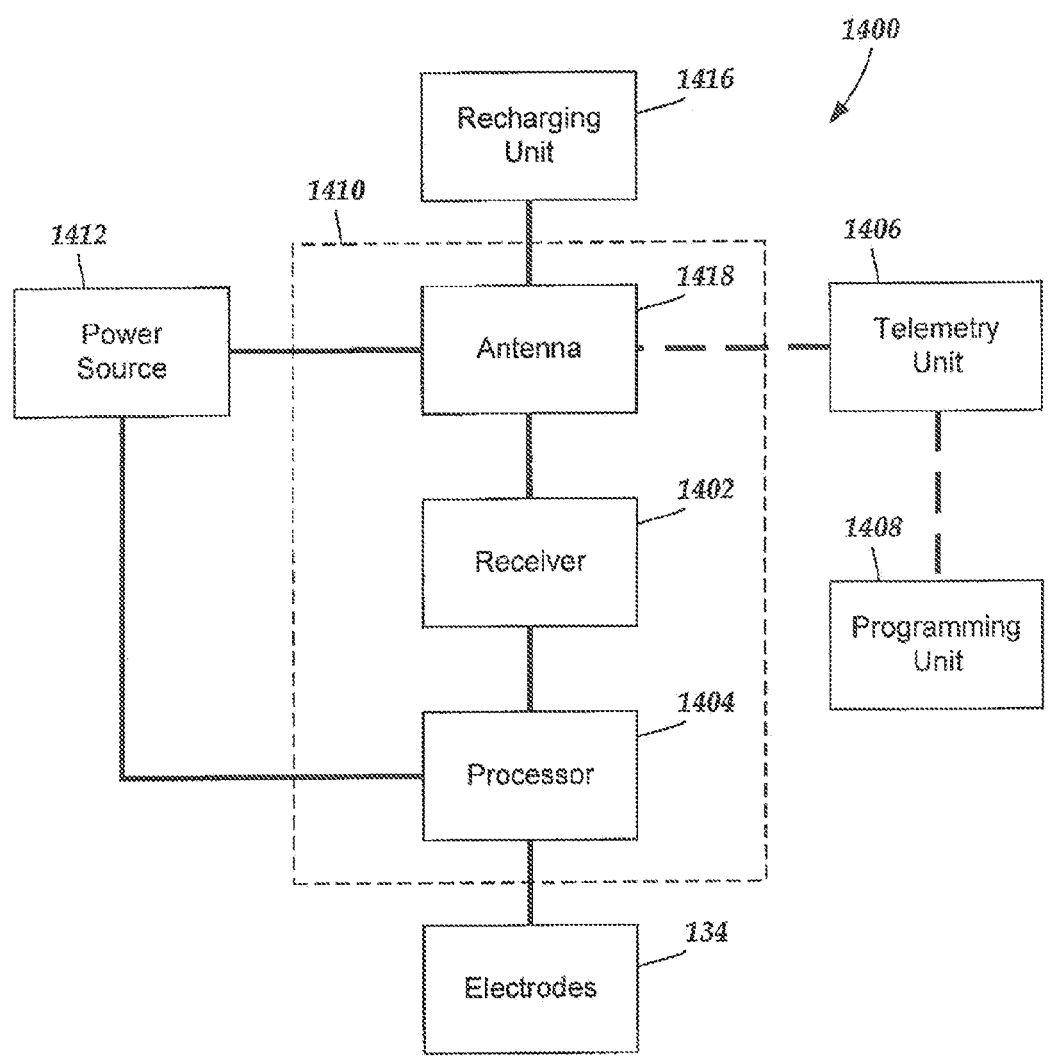
FIG. 14 is a schematic overview of one embodiment of components of a stimulation system, including an electronic subassembly disposed within a control module, according to the invention.

FIG. 14 is a schematic overview of one embodiment of components of an electrical stimulation system 1400 including an electronic subassembly 1410 disposed within a control module. It will be understood that the electrical stimulation system can include more, fewer, or different components and can have a variety of different configurations including those configurations disclosed in the stimulator references cited herein.

Some of the components (for example, power source 1412, antenna 1418, receiver 1402, and processor 1404) of the electrical stimulation system can be positioned on one or more circuit boards or similar carriers within a sealed housing of an implantable pulse generator, if desired. Any power source 1412 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. Patent Application Publication No. 2004/0059392, incorporated herein by reference.

As another alternative, power can be supplied by an external power source through inductive coupling via the optional antenna 1418 or a secondary antenna. The external power source can be in a device that is mounted on the skin of the user or in a unit that is provided near the user on a permanent or periodic basis.

If the power source 1412 is a rechargeable battery, the battery may be recharged using the optional antenna 1418, if desired. Power can be provided to the battery for recharging by inductively coupling the battery through the antenna to a recharging unit 1416 external to the user. Examples of such arrangements can be found in the references identified above.

In one embodiment, electrical current is emitted by the electrodes 134 on the paddle or lead body to stimulate nerve fibers, muscle fibers, or other body tissues near the electrical stimulation system. A processor 1404 is generally included to control the timing and electrical characteristics of the electrical stimulation system. For example, the processor 1404 can, if desired, control one or more of the timing, frequency, strength, duration, and waveform of the pulses. In addition, the processor 1404 can select which electrodes can be used to provide stimulation, if desired. In some embodiments, the processor 1404 may select which electrode(s) are cathodes and which electrode(s) are anodes. In some embodiments, the processor 1404 may be used to identify which electrodes provide the most useful stimulation of the desired tissue.

Any processor can be used and can be as simple as an electronic device that, for example, produces pulses at a regular interval or the processor can be capable of receiving and interpreting instructions from an external programming unit 1408 that, for example, allows modification of pulse characteristics. In the illustrated embodiment, the processor 1404 is coupled to a receiver 1402 which, in turn, is coupled to the optional antenna 1418. This allows the processor 1404 to receive instructions from an external source to, for example, direct the pulse characteristics and the selection of electrodes, if desired.

In one embodiment, the antenna 1418 is capable of receiving signals (e.g., RF signals) from an external telemetry unit 1406 which is programmed by a programming unit 1408. The programming unit 1408 can be external to, or part of, the telemetry unit 1406. The telemetry unit 1406 can be a device that is worn on the skin of the user or can be carried by the user and can have a form similar to a pager, cellular phone, or remote control, if desired. As another alternative, the telemetry unit 1406 may not be worn or carried by the user but may only be available at a home station or at a clinician's office. The programming unit 1408 can be any unit that can provide information to the telemetry unit 1406 for transmission to the electrical stimulation system 1400. The programming unit 1408 can be part of the telemetry unit 406 or can provide signals or information to the telemetry unit 1406 via a wireless or wired connection. One example of a suitable programming unit is a computer operated by the user or clinician to send signals to the telemetry unit 1406.

The signals sent to the processor 1404 via the antenna 1418 and receiver 1402 can be used to modify or otherwise direct the operation of the electrical stimulation system. For example, the signals may be used to modify the pulses of the electrical stimulation system such as modifying one or more of pulse duration, pulse frequency, pulse waveform, and pulse strength. The signals may also direct the electrical stimulation system 1400 to cease operation, to start operation, to start charging the battery, or to stop charging the battery. In other embodiments, the stimulation system does not include an antenna 1418 or receiver 1402 and the processor 1404 operates as programmed.

Optionally, the electrical stimulation system 1400 may include a transmitter (not shown) coupled to the processor 1404 and the antenna 1418 for transmitting signals back to the telemetry unit 1406 or another unit capable of receiving the signals. For example, the electrical stimulation system 1400 may transmit signals indicating whether the electrical stimulation system 1400 is operating properly or not or indicating when the battery needs to be charged or the level of charge remaining in the battery. The processor 1404 may also be capable of transmitting information about the pulse characteristics so that a user or clinician can determine or verify the characteristics.

The above specification, examples and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. A lead connection system comprising:
   a connector housing having a first end, a second end opposite to the first end, a first side, and a second side opposite to the first side;
   a first lead retainer disposed along the first side of the connector housing, the first lead retainer configured and arranged to receive a first lead of the plurality of leads, the first lead retainer comprising a first pivotable hinged panel that cooperates with the connector housing to removably retain the first lead when pivoted to a closed position, and
   a second lead retainer disposed along the second side of the connector housing, the second lead retainer configured and arranged to receive a second lead of the plurality of leads, the second lead retainer comprising a second pivotable hinged panel that cooperates with the connector housing to removably retain the second lead when pivoted to a closed position;
   a first plurality of connector contacts disposed along the first side of the connector housing, the first plurality of connector contacts configured and arranged for electrically coupling with a plurality of terminals disposed along a proximal end portion of the first lead when the first lead is received by the first lead retainer and the first pivotable hinged panel is pivoted to the closed position;
   a second plurality of connector contacts disposed along the second side of the connector housing, the second plurality of connector contacts configured and arranged for electrically coupling with a plurality of terminals disposed along a proximal end portion of the second lead when the second lead is received by the second lead retainer and the second pivotable hinged panel is pivoted to the closed position; and
   a connector cable having a proximal end and a distal end, the distal end electrically coupled to each of the first plurality of connector contacts and the second plurality of connector contacts, the proximal end configured and arranged for coupling to a trial stimulator.

2. The lead connection system of claim 1, wherein the first lead retainer comprises at least one cantilever snap-fit boss and at least one undercut notch, and wherein the first lead retainer is configured and arranged for removably retaining the first lead within the first lead retainer via a snap fit between the at least one cantilever snap-fit boss and the at least one undercut notch when the first pivotable hinged panel is pivoted to the closed position.

3. The lead connection system of claim 1, wherein the first lead retainer is configured and arranged to removably retain the first lead with portions of the first lead extending from the first end of the connector housing.

4. The lead connection system of claim 1, wherein the first lead retainer comprises a plurality of spaced-apart lead-retention members disposed along an inner surface of the first pivotable hinged panel.

5. The lead connection system of claim 4, wherein the connector housing further comprises a plurality of spaced-apart lead-retention members disposed along an inner surface of the first side of the connector housing.

6. The lead connection system of claim 5, wherein the first lead retainer is configured and arranged to removably retain the first lead by sandwiching the first lead between the plurality of lead-retention members of the inner surface of the first pivotable hinged panel and the plurality of lead-retention members of the first side of the connector housing when the first pivotable hinged panel is pivoted to the closed position.

7. The lead connection system of claim 1, wherein the first plurality of connector contacts are disposed along a first contact element, the first contact element configured and arranged to place the first plurality of connector contacts in an arrangement that aligns with the plurality of terminals of the first lead when the first lead is retained by the first lead retainer.

8. The lead connection system of claim 1, further comprising at least one printed circuit board disposed in the connector housing, the at least one printed circuit board electrically coupled to the connector cable and to the first plurality of connector contacts.

9. An electrical-stimulator testing kit comprising:
   the lead connection system of claim 1; and
   a trial stimulator electrically coupleable to the proximal end of the connector cable of the lead connection system, the trial stimulator configured and arranged for providing electrical signals to the plurality of retained leads.

10. A lead assembly comprising:
    the lead connection system of claim 1; and
    a plurality of leads comprising a first lead and a second lead, each lead of the plurality of leads having a proximal end portion and a distal end portion, each lead of the plurality of leads comprising
    a plurality of electrodes disposed along the distal end portion of the lead,
    a plurality of terminals disposed along the proximal end portion of the lead, and
    a plurality of conductor wires extending along the lead and coupling the plurality of electrodes to the plurality of terminals.

11. The lead assembly of claim 10, further comprising a first stylet insertable into the proximal end portion of the first lead and extendable therefrom when the first lead is retained by the first lead retainer.

12. The lead assembly of claim 11, wherein the first lead retainer of the lead connection system is configured and arranged to removably retain the first lead with the first stylet extending from the second end of the connector housing when the first stylet is inserted into the proximal end portion of the first lead.

13. The lead assembly of claim 11, wherein the first lead retainer of the lead connection system is configured and arranged to removably retain the first lead with the first stylet extending from the second end of the connector housing such that the first stylet is usable to guide the distal end portion of the first lead while the first lead is retained by the first lead retainer.

14. The lead assembly of claim 10, further comprising a second stylet insertable into the proximal end portion of the second lead and extendable therefrom when the second lead is retained by the second lead retainer.

15. The lead assembly of claim 14, wherein the second lead retainer of the lead connection system is configured and arranged to removably retain the second lead with the second stylet extending from the second end of the connector housing when the second stylet is inserted into the proximal end portion of the second lead.

16. A method for stimulating patient tissue, the method comprising:
    providing the lead connection system of claim 1;
    advancing a distal end portion of a first lead into a patient, the first lead comprising a plurality of electrodes disposed along the distal end portion of the first lead and a plurality of terminals disposed along a proximal end portion of the first lead;
    disposing the proximal end portion of the first lead into the first lead retainer of the lead connection system;
    pivoting the first pivotable hinged panel of the first lead retainer to a closed position to removably retain the first lead within the first lead retainer;
    inserting the proximal end of the connector cable into a trial stimulator; and
    providing electrical signals from the trial stimulator to the plurality of electrodes of the first lead.

17. The method of claim 16, further comprising inserting a first stylet into the proximal end portion of the first lead with a portion of the stylet extending outwardly from the proximal end portion of the first lead.

18. The method of claim 17, further comprising moving the distal end portion of the first lead using the portion of the first stylet extending outwardly from the proximal end portion of the first lead while the first lead is retained by the first lead retainer.

19. The method of claim 17, wherein the step of inserting a first stylet into the proximal end portion of the first lead with a portion of the stylet extending outwardly from the proximal end portion of the first lead occurs prior to the step of disposing the proximal end portion of the first lead into the first lead retainer of the lead connection system.

20. The method of claim 16, further comprising advancing a distal end portion of a second lead into a patient, the second lead comprising a plurality of electrodes disposed along the distal end portion of the second lead and a plurality of terminals disposed along a proximal end portion of the second lead;
    disposing the proximal end portion of the second lead into the second lead retainer of the lead connection system; and
    pivoting the second pivotable hinged panel of the second lead retainer to a closed position to removably retain the second lead within the second lead retainer.

* * * * *